US011195619B2

(12) United States Patent
Baughman et al.

(10) Patent No.: US 11,195,619 B2
(45) Date of Patent: Dec. 7, 2021

(54) REAL TIME SENSOR ATTRIBUTE DETECTION AND ANALYSIS

(71) Applicant: INTERNATIONAL BUSINESS MACHINES CORPORATION, Armonk, NY (US)

(72) Inventors: Aaron K. Baughman, Silver Spring, MD (US); Gary F. Diamanti, Wake Forest, NC (US); Patrick Rodrigo Mardones Rodriguez, Recoleta (CL); Mauro Marzorati, Lutz, FL (US)

(73) Assignee: International Business Machines Corporation, Armonk, NY (US)

( * ) Notice: Subject to any disclaimer, the term of this patent is extended or adjusted under 35 U.S.C. 154(b) by 214 days.

(21) Appl. No.: 16/133,931

(22) Filed: Sep. 18, 2018

(65) Prior Publication Data

US 2020/0090809 A1 Mar. 19, 2020

(51) Int. Cl.
*G16H 50/20* (2018.01)
*G16H 50/30* (2018.01)
*G06N 20/00* (2019.01)
*G06F 1/16* (2006.01)

(52) U.S. Cl.
CPC .............. *G16H 50/20* (2018.01); *G06N 20/00* (2019.01); *G16H 50/30* (2018.01); *G06F 1/163* (2013.01)

(58) Field of Classification Search
CPC ........ G16H 50/20; G16H 50/30; G06N 20/00; G06F 1/163
See application file for complete search history.

(56) References Cited

U.S. PATENT DOCUMENTS

2013/0245396 A1 9/2013 Berman
2013/0262356 A1* 10/2013 Bonastre .............. G06K 9/6215
706/20

(Continued)

FOREIGN PATENT DOCUMENTS

WO 2015127441 A1 8/2015

OTHER PUBLICATIONS

Apple iPhone User's Guide, 2007, p. 114 (Year: 2007).*
Genard, Gary, How to Use Video to Boost Your Speaking Credibility and Charisma, The Genard Method, Nov. 2, 2014 (Year: 2014).*

(Continued)

*Primary Examiner* — Jonathan Durant
*Assistant Examiner* — Anne-Marie K Alderson
(74) *Attorney, Agent, or Firm* — Schmeiser, Olsen & Watts; Erik C. Swanson

(57) ABSTRACT

A method and system for improving real-time audio, video, and sensor detection and analysis is provided. The method includes retrieving audio/video data, biometric data, and environmental data associated with associated with a user at a location. The audio/video data, biometric data, and environmental data are analyzed and based on the analysis, a current biometric state of the user is determined. The current biometric state of the user is compared to a baseline biometric state of the user and it is determined that the current biometric state comprises an elevated biometric state with respect to the baseline biometric state of the user. Self-learning software code for executing a machine based interaction modification event associated with reducing the elevated biometric state of the user is generated and the machine based interaction modification event is executed.

20 Claims, 7 Drawing Sheets

(56) References Cited

U.S. PATENT DOCUMENTS

| | | | |
|---|---|---|---|
| 2014/0278220 A1* | 9/2014 | Yuen | A61B 5/4812 |
| | | | 702/150 |
| 2016/0054023 A1* | 2/2016 | Baker | G05B 15/02 |
| | | | 307/31 |
| 2016/0217807 A1 | 7/2016 | Gainsboro | |
| 2016/0363914 A1 | 12/2016 | Kim | |
| 2018/0165854 A1* | 6/2018 | Du | G06F 3/011 |
| 2018/0254097 A1* | 9/2018 | Gani | G16H 20/70 |
| 2019/0038185 A1* | 2/2019 | Arnold | A61B 5/7278 |

OTHER PUBLICATIONS

Graham, Susan L. et al; An Improved Context-Free Recognizer; ACM Transactions on Programming Languages and Systems, vol. 2, No. 3; Jul. 1980; pp. 415-462.

Minelli, Roberto et al; I Know What Your Did Last Summer: An Investigation of How Developers Spend Their Time; 2015 IEEE 23rd International Conference on Program Comprehension; May 18-19, 2015; pp. 25-35.

Rosenberg, Louis B.; Human Swarming, a real-time method for Parallel Distributed Intelligence; 2015 Swarm/Human Blended Intelligence Workshop (SHBI); Sep. 28-29, 2015; 7 pages.

Yokota, Sho et al; Motion Design of Service Robot—Study on Human Impression; 2015 12th IEEE International Conference on Industrial Informatics; Jul. 27-30, 2014; pp. 770-774.

Mell, Peter et al.; "The NIST Definition of Cloud Computing;" National Institute of Standards and Technology; Special Publication 800-145; Sep. 2011; 7 pages.

* cited by examiner

REAL TIME SENSOR ATTRIBUTE DETECTION AND ANALYSIS

FIELD

The present invention relates generally to a method for detecting sensor based attributes and in particular to a method and associated system for improving wearable device hardware and software technology associated with sensor triggered events by automatically retrieving sensor based data and executing a machine based interaction modification event resulting in a reduction of an elevated biometric state of a user for learning purposes.

BACKGROUND

Accurately detecting and analyzing retrieved attributes includes an inaccurate process with little flexibility. Determining and rectifying elevated user states may include a complicated process that may be time consuming and require a large amount of resources. Wearable devices typically monitor biometric functions of a user for presentation. Typical user behavior may be modified in accordance with a physiological state of the user.

SUMMARY

A first aspect of the invention provides a method comprising: retrieving in real time, by a processor of a wearable hardware device via an audio/video retrieval device of the wearable hardware device, audio/video data associated with a user at a location; retrieving in real time, by the processor via biometric sensors of the wearable hardware device, biometric data associated with the user; retrieving in real time, by the processor via environmental sensors of the wearable hardware device, environmental data associated with the location of the user; analyzing, by the processor, the audio/video data, the biometric data, and the environmental data; determining, by the processor based on results of the analyzing, a current biometric state of the user; comparing, by the processor, the current biometric state of the user to a baseline biometric state of the user; determining, by the processor based on results of the comparing, that the current biometric state of the user comprises an elevated biometric state with respect to the baseline biometric state of the user; generating, by the processor, self-learning software code for executing a machine based interaction modification event associated with reducing the elevated biometric state of the user; and executing, by the processor executing the self-learning software code, the machine based interaction modification event resulting in a reduction of the elevated biometric state of the user.

A second aspect of the invention provides a computer program product, comprising a computer readable hardware storage device storing a computer readable program code, the computer readable program code comprising an algorithm that when executed by a processor of a wearable hardware device implements a method, the method comprising: retrieving in real time, by the processor via an audio/video retrieval device of the wearable hardware device, audio/video data associated with a user at a location; retrieving in real time, by the processor via biometric sensors of the wearable hardware device, biometric data associated with the user; retrieving in real time, by the processor via environmental sensors of the wearable hardware device, environmental data associated with the location of the user; analyzing, by the processor, the audio/video data, the biometric data, and the environmental data; determining, by the processor based on results of the analyzing, a current biometric state of the user; comparing, by the processor, the current biometric state of the user to a baseline biometric state of the user; determining, by the processor based on results of the comparing, that the current biometric state of the user comprises an elevated biometric state with respect to the baseline biometric state of the user; generating, by the processor, self-learning software code for executing a machine based interaction modification event associated with reducing the elevated biometric state of the user; and executing, by the processor executing the self-learning software code, the machine based interaction modification event resulting in a reduction of the elevated biometric state of the user.

A third aspect of the invention provides a wearable hardware device comprising a processor coupled to a computer-readable memory unit, the memory unit comprising instructions that when executed by the computer processor implements a method comprising: retrieving in real time, by the processor via an audio/video retrieval device of the wearable hardware device, audio/video data associated with a user at a location; retrieving in real time, by the processor via biometric sensors of the wearable hardware device, biometric data associated with the user; retrieving in real time, by the processor via environmental sensors of the wearable hardware device, environmental data associated with the location of the user; analyzing, by the processor, the audio/video data, the biometric data, and the environmental data; determining, by the processor based on results of the analyzing, a current biometric state of the user; comparing, by the processor, the current biometric state of the user to a baseline biometric state of the user; determining, by the processor based on results of the comparing, that the current biometric state of the user comprises an elevated biometric state with respect to the baseline biometric state of the user; generating, by the processor, self-learning software code for executing a machine based interaction modification event associated with reducing the elevated biometric state of the user; and executing, by the processor executing the self-learning software code, the machine based interaction modification event resulting in a reduction of the elevated biometric state of the user.

The present invention advantageously provides a simple method and associated system capable of accurately detecting and analyzing retrieved attributes.

DETAILED DESCRIPTION

Figure 1:
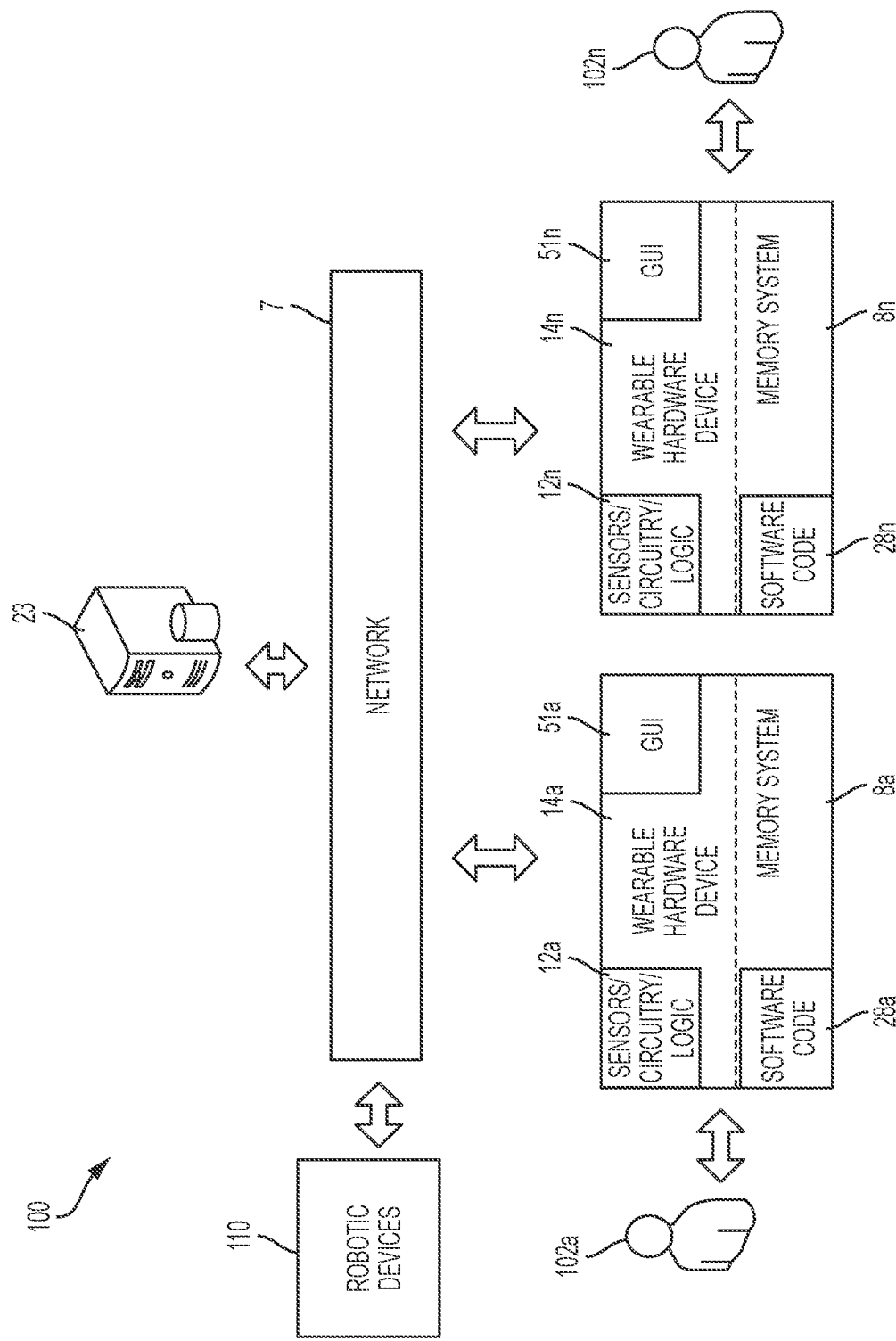
FIG. 1 illustrates a system improving wearable device hardware and software technology associated with sensor triggered events by automatically retrieving sensor based data and executing a machine based interaction modification event resulting in a reduction of an elevated biometric state of a user, in accordance with embodiments of the present invention.

FIG. 1 illustrates a system 100 for improving wearable device hardware and software technology associated with sensor triggered events by automatically retrieving sensor based data and executing a machine based interaction modification event resulting in a reduction of an elevated biometric state of a user, in accordance with embodiments of the present invention. Typical (human) group interactions produce varied results among each of its members. Social skills and experiences comprise key attributes for interacting and functioning successfully within group structures. The ability to analyze real life group interactions and experiences for training interactions and improving member (i.e., of the group) experiences and outcomes provides huge benefits for members of the group users. Additionally, dynamically replaying audio and video presenting scenarios allow users to adaptively learn how to avoid negative aspects of group interactions. Likewise, dynamically replaying the aforementioned audio and video allows the users to optimize positive aspects of group interactions. Therefore, system 100 enables a process for generating and executing self-learning software code for enabling adaptive learning techniques based on detected human emotion by replaying human group social interactions for optimizing experiences and learned interactions thereby improving user social skills and experiences.

System 100 is configured to enable wearable hardware devices 14a . . . 14n to capture real time group interactions (e.g., via audio data, video data, etc.) and a biometric state (e.g., via biometrics data, environmental data, etc.) of a user to adaptively learn interactions of the user. Subsequently, self-learning software code is generated for generating suggestions for modifying interactions of the user via usage of specialized cognitive hardware and software systems. System 100 enables the following process for generating the aforementioned self-learning software code:

1. Group interactions (of a group of users such as users 102a . . . 102n) are captured via a plurality of sensors of wearable hardware devices 14a . . . 14n. The captured group interactions are analyzed for determining a current biometric state (e.g., agitated, stressed, tired, attentive, comfortable, happy, embarrassed, etc.) of users 102a . . . 102n of wearable hardware devices 14a . . . 14n.

2. Elevated state changes with respect to a biometric state of the user are determined for generating an event set.

3. The event set is processed and self-learning software code is generated for generating recommendations for changes in interaction patterns (of users 102a . . . 102n) for reducing the effects of an undesirable situation or heightening the effects of a desired situation. Subsequently, users 102a . . . 102n are monitored (via sensors/circuitry/logic 12a . . . 12n) for interaction pattern changes.

4. The scenario or event involving interactions with groups of people are reproduced virtually by recreating digital patterns for users 102a . . . 102n to analyze experiences during the interactions and learning and improve social skills of users 102a . . . 102n.

System 100 of FIG. 1 includes a server hardware device (or hardware system) 23 connected through a network 7 to wearable hardware devices 14a . . . 14n associated with users 102a . . . 102n. Additionally, server hardware device 23 may be connected through network 7 to robotic devices 110. Wearable hardware device 14a comprises sensors/circuitry/logic 12a, a graphical user interface (GUI) 51a, and a (specialized) memory system 8a. Memory system 8a comprises (self-learning) software code 28a. Memory system 8a may include a single memory system. Alternatively, memory system 8a may include a plurality of memory systems. Wearable hardware device 14n comprises sensors/circuitry/logic 12n, a GUI 51n, and a (specialized) memory system 8n. Memory system 8n comprises software code 28n. Memory system 8n may include a single memory system. Alternatively, memory system 8n may include a plurality of memory systems. Server hardware device 23 and wearable hardware devices 14a . . . 14n each may comprise an embedded device. An embedded device is defined herein as a dedicated device or computer comprising a combination of computer hardware and software (fixed in capability or programmable) specifically designed for executing a specialized function. Programmable embedded computers or devices may comprise specialized programming interfaces. In one embodiment, server hardware device 23 and wearable hardware devices 14a . . . 14n may each comprise a specialized hardware device comprising specialized (non-generic) hardware and circuitry (i.e., specialized discrete non-generic analog, digital, and logic based circuitry) for (independently or in combination) executing a process described with respect to FIGS. 1-7. The specialized discrete non-generic analog, digital, and logic based circuitry (e.g., sensors/circuitry/logic 12a . . . 12n, etc.) may include proprietary specially designed components (e.g., a specialized integrated circuit, such as for example an Application Specific Integrated Circuit (ASIC) designed for only implementing an automated process for improving wearable device hardware and software technology associated with sensor triggered events by automatically retrieving sensor based data and executing a machine based behavioral modification event resulting in a reduction of an elevated physiological state of a user thereby improving a current physiological state of the user. Sensors/circuitry/logic 12a . . . 12n may include any type of internal or external sensors including, inter alia, GPS sensors, social network code based sensors, environmental sensors, biometric sensors, voltage sensors, network traffic sensors, temperature sensors, audio/video retrieval devices, heartrate sensors, ultrasonic sensors, pressure sensors, light/optical sensors, blood pressure sensors, weather sensors, etc. Wearable hardware devices 14a . . . 14n may include, inter alia, smart watches, activity trackers, smart computer based eyewear, wearable computers, wearable smart phones, etc. Network 7 may include any type of network including, inter alia, a local area network, (LAN), a wide area network (WAN), the Internet, a wireless network, etc.

Wearable hardware devices 14a ... 14n are enabled to capture (via sensors/circuitry/logic 12a ... 12n) and record real time group formation dynamics and detailed personal interactions within a group of users 102a ... 102n. The recorded group formation dynamics and detailed personal interactions in combination with detailed vital statistics associated with user experiences is inputted as training data for generating self-learning software code 28a ... 28n.

System 100 is enabled to detect if users 102a ... 102n are associated with an elevated biometric state (e.g., an uncomfortable awkward situation, or a high energy fun sporting situation, etc.) via execution of hardware sensors and self-learning software code to retrieve numerous inputs and data leading up to the aforementioned situations. The gathered input and data is digitized to virtually reproduce or replay the experiences and provide potential alternate choices for a better perceived outcome. Users 102a ... 102n may replay the virtual reproductions with additional groups of people for virtually recreating similar patterns to garner the experience of associated interactions. During the replay process, users 102a ... 102n are enabled to pause a virtual replay and system 100 generates software code for providing potential suggestions via a GUI (e.g., virtual smart eyewear) with respect to approaching the interactions. For example, system 100 may generate virtual presentations for: mimicking positive interactions, focusing on reducing bad feelings produced from an awkward situation, etc. The virtual presentations may allow users 102a ... 102n to improve social skills within simple or complex group dynamics. Additionally, users 102a ... 102n and robotic devices 110 may be participants in groups and events such that both users 102a ... 102n and robotic devices 110 may learn from captured behavior and virtually modeled presentations. A session may be terminated if a user is detected to experience a same discomfort and doesn't learn from the virtually presented event. Likewise, the virtual presentation may be presented again after user vital signs have been detected at normal levels.

Wearable hardware devices 14a ... 14n comprise special purpose hardware for executing special purpose programmable logic. Additionally, wearable hardware devices 14a ... 14n comprise integrated sensors (e.g., sensors/circuitry/logic 12a ... 12n) for detecting and capturing environmental detectable conditions (e.g., temperature, aural, visual, tactile, music vs noise, loudness level, ambient light level, strobe/flashing effects, galvanic skin response, etc.) surrounding users 102a ... 102n. The environmental detectable conditions are analyzed to determine biometric states of users 102a ... 102n. Biometric states may include logical digital constructs that accurately describe human or robotic biometric state in terms of several key metrics such, inter alia, an agitated state, a stressed state, a tired state, an attentive state, a comfortable state, a happy state, an embarrassed state, a comfort level, etc. The logical digital constructs comprise therefore an N-tuple vector of numeric values and a textual description field. An event set is defined herein as a logical construct accurately describing a series of events and a resulting biometric state that a human or robotic cognitive agent experienced during a given timeframe.

Figure 2:
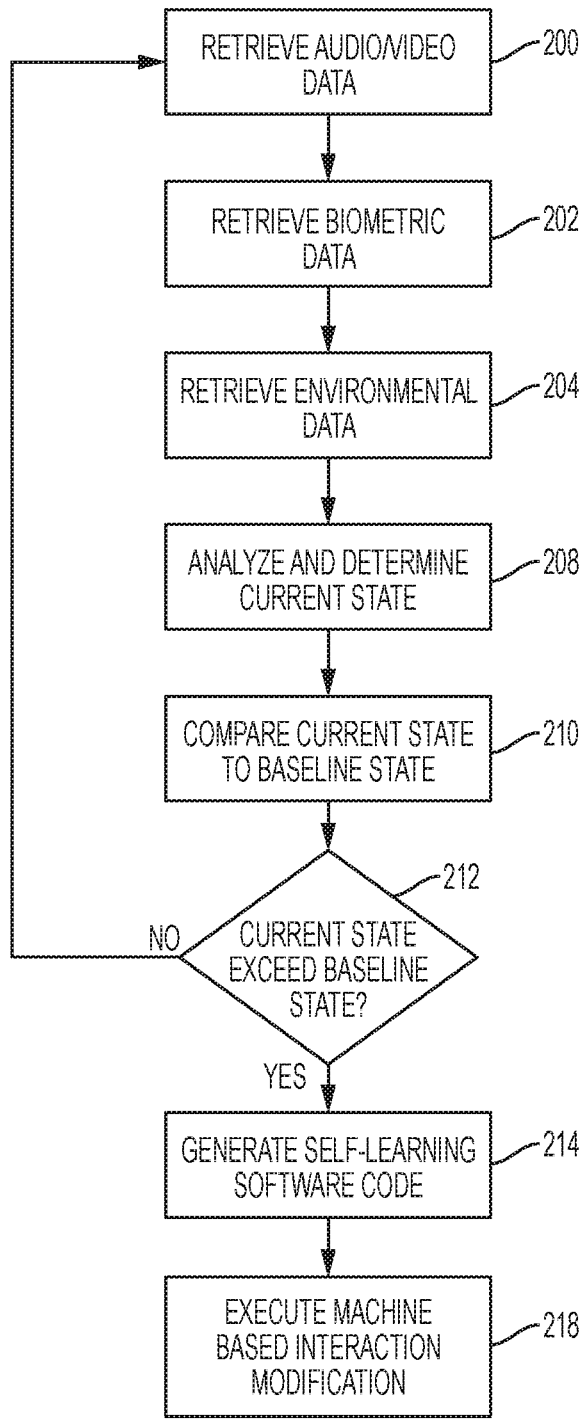
FIG. 2 illustrates an algorithm detailing a process flow enabled by the system of FIG. 1 for improving wearable device hardware and software technology associated with sensor triggered events by automatically retrieving sensor based data and executing a machine based interaction modification event resulting in a reduction of an elevated biometric state of a user, in accordance with embodiments of the present invention.

FIG. 2 illustrates an algorithm detailing a process flow enabled by system 100 of FIG. 1 for improving wearable device hardware and software technology associated with sensor triggered events by automatically retrieving sensor based data and executing a machine based interaction modification event resulting in a reduction of an elevated biometric state of a user thereby improving a current biometric state of the user, in accordance with embodiments of the present invention. Each of the steps in the algorithm of FIG. 2 may be enabled and executed in any order by a computer processor(s) executing computer code. Additionally, each of the steps in the algorithm of FIG. 2 may be enabled and executed in combination by server hardware device 23 and wearable hardware devices 14a ... 14n of FIG. 1. In step 200, audio/video data associated with a user at a location is retrieved in real time via an audio/video retrieval device of a wearable hardware device. In step 202, biometric data associated with the user is retrieved in real time via biometric sensors of the wearable hardware device. Biometric data may include, inter alia, a current respiration rate of the user, a current body temperature of the user, a current perspiration rate of the user, and a current heartrate of the user, etc. In step 204, environmental data associated with a location of the user is retrieved in real time via environmental sensors of the wearable hardware device. The environmental data may include, inter alia, noise level conditions, temperature level conditions, lighting level conditions, humidity level conditions, etc.

In step 208, the audio/video data, the biometric data, and the environmental data are analyzed and a current biometric state for the user is determined based on the analysis. Analysis of the aforementioned data (e.g., an event set) may include usage of recursive neural network machine learning techniques for generating recommendations for changes in interactions. Recursive neural network machine learning techniques may include, inter alia, gaussian mixture model (GMM) techniques and hidden markov model (HMM) techniques. A GMM technique enables probability distributions within biometric systems (e.g., vocal tract related effects in a speech recognition system). An HMM technique determines user states and predicts next state of a user via probability distribution. In step 210, the current biometric state of the user is compared to a baseline biometric state of the user. In step 212, it is determined if the current biometric state of the user comprises an elevated biometric state with respect to the baseline biometric state of the user. If in step 212, it is determined that the current biometric state of the user does not comprise an elevated biometric state with respect to the baseline biometric state of the user then step 200 is repeated to continue the monitoring process. If in step 212, it is determined that the current biometric state of the user does comprise an elevated biometric state with respect to the baseline biometric state of the user then in step 214, self-learning software code for executing a machine based interaction modification event associated with reducing the elevated biometric state of the user is generated such that any retrieved input data may be reproduced or replayed to present a view of an experience for the user for providing alternate choices for a perceived better interaction based outcome. Additional users may replay the experience and generate additional feedback for incorporating into a recommendation provided by the system. The machine based interaction modification event may be implemented as a neural network (e.g., a convolutional neural network, a recurrent neural network, etc.). The neural network is responsible for receiving captured events and generating predictions with respect to how a user could have achieved a desired outcome with respect to an interaction modification scenario being reviewed or portrayed. Therefore, the learned interaction modifications from the predictions lead to a desired outcome change. For example, a scenario being reviewed made a user uncomfortable. Therefore, the machine based interaction modification system is configured to generate predictions (e.g., a list of ranked recommendations) for actions that may change the users' interactions such that the actions influence a desired outcome within the scenario. The following process illustrates and implementation example describing a conference call scenario initiated with four participants:

The four participants are as follows: participant 1 (P1) is a support engineer, participant 2 (P2) is a support manager, participant 3 (p3) is a director, and participant 4 (p4) is a remotely located engineer. The process is initiated when P1 has been asked to join a meeting in a conference room for presentation of detail regarding a customer escalation event. Likewise, P1, P2, and P3 are all in the conference room using a collaboration tool for access to real-time video and voice functionality (via a network) for communications with remotely located P4. The communication session begins for P1 (i.e., accessing the collaboration tool and using a wearable hardware device that capturing video, voice, and biometric data for P1, P2, P3, and P4) and P1 is asked to summarize a latest status (for the customer escalation event) reported by P3. Subsequently, P1 starts to talk and is immediately interrupted by P3 with several back to back questions. Additionally, P2 (i.e., P1's direct manager) begins to show visible signs of nervousness (e.g., wringing his hands and moving around nervously in his chair). Likewise, as P1 starts to describe the customer escalation event and begins to stutter and perspire as he speaks, an event set associated with P1's biometrics rising is generated. P1 further answers P3's questions and the focus of P3 is directed to P2. P2 is not aware of a latest status of the customer escalation event and all participants are able to hear the apprehension P2's voice in combination with detecting an increase in a level of nervous movement and therefore an additional event set is generated. P1 is able to observe the aforementioned interaction and appears to become agitated since P2 is his manager. In response, sentiment and tone analysis code (running on P1's wearable hardware device) illustrates that P3 is negative with respect to the situation. Likewise, P4 notices these visible queues from the video cast and speaks up with crisp answers to P3's questions. P4 is able to respond with confidence and P3 begins to calm down thereby generating a further event set capturing a noticeable change in interactions. P4 continues to add details and status updates and the sentiment and tone analysis code determines that P3's communication begins to shift to a more positive communication. P1 is further called on for a question by P3 and P1 is now able to better answer any questions with less visible distress. Additionally, P1 is producing more positive biometrics as P4 has a very calming influence and was able to influence the tone of the call thereby generating another event set. P1 begins to calm downs but is still in a biometric elevated state. P3 states that there is another meeting in 2 hours to retrieve a latest status. P2 ends the call and everyone leaves the room and the session and collaboration ends. The meeting ends and the system generates a set of predictions based on all of the generated events sets and details of the conference call. Subsequently, P1 goes back to their office to retrieve a latest status from the customer. P1 is currently using the wearable hardware device and replays the entire meeting and reviews the generated predictions to learn how to influence the outcome of similar future meetings. For example, P1 while watching P3's interactions on the meeting replay, reviews the recommendations from the system to alter the outcome. These predictions and recommendations include a change in posture, direct eye contact with P3, and short crisp answers. Likewise, P1 observes how P4 interacts and how that interaction helped to change the tone of the call, taking cues from P4's approach. P1 will use this feedback when participating in the next call.

In step 218, the machine based interaction modification event is executed (via execution of self-learning software code) resulting in a reduction of the elevated biometric state of the user thereby improving the current biometric state of the user. As a first example, executing the machine based interaction modification event may include: generating recommendations for the user to reduce the elevated biometric state; and presenting the recommendations to the user via a specialized GUI. As a second example, executing the machine based interaction modification event may include: generating a visual simulation associated with the audio/video data; and presenting the visual (e.g., virtual) simulation to the user via a specialized GUI for enabling the user to reduce the elevated biometric state. As a third example, executing the machine based interaction modification event may include: automatically modifying a temperature control setpoint for an HVAC system and/or automatically modifying a lighting level at the location of the user.

Figure 3:
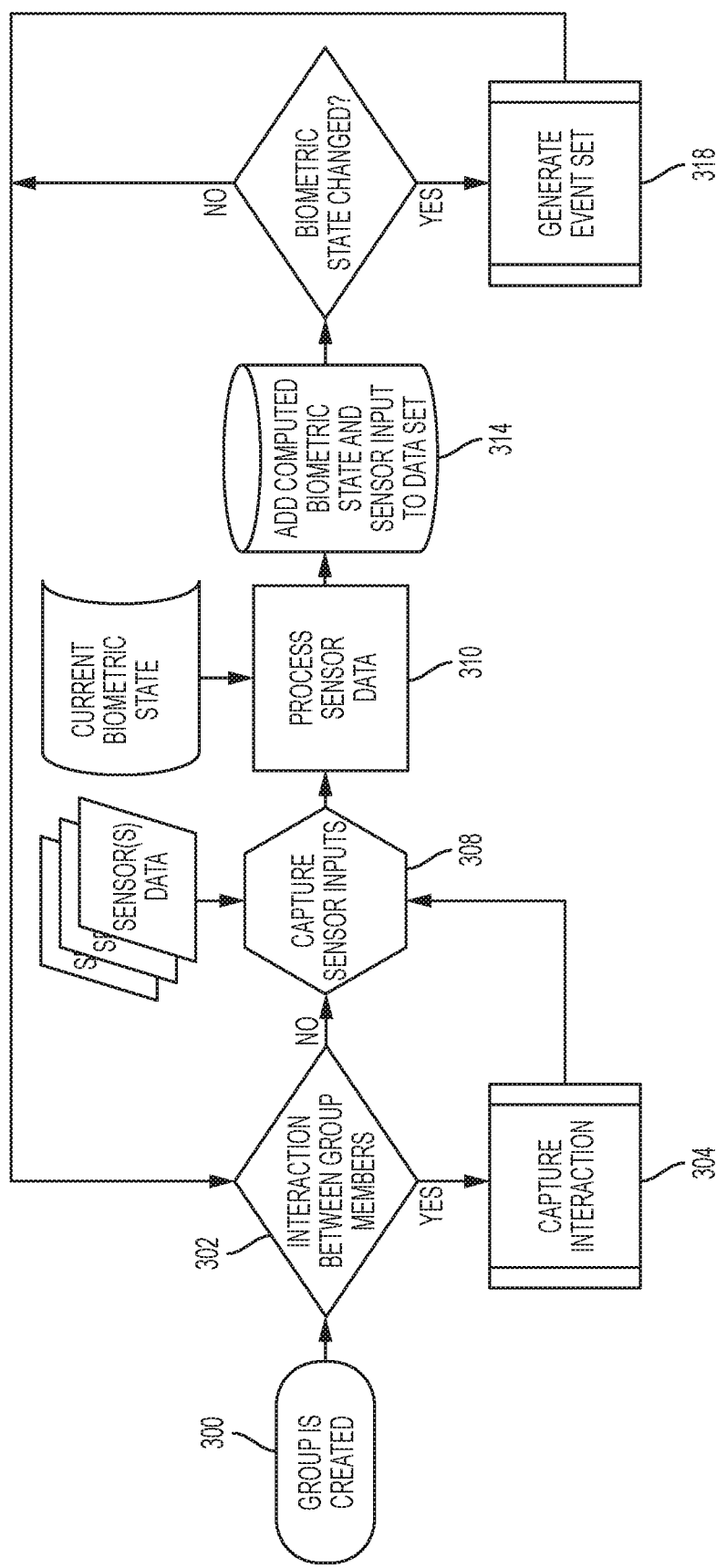
FIG. 3 illustrates an algorithm detailing a process flow enabled by the system of FIG. 1 for capturing and creating an event set for improving real time biometric state analysis, in accordance with embodiments of the present invention.

FIG. 3 illustrates an algorithm detailing a process flow enabled by system 100 of FIG. 1 for capturing and creating an event set for improving real time biometric state analysis, in accordance with embodiments of the present invention. In step 300, the process is initiated when a user possessing a wearable device joins and participates in a self-organized group and interactions between group members are detected in step 302. In step 304, the user's wearable device records interactions and group dynamics from its own point of view. In step 308, the user's wearable device continually records and processes (in step 310) sensor inputs and maintains a determined user biometric state. Upon detection of a significant change in one or more of key metrics or a determined biometric state, the wearable device packages (in step 314) sensed conditions into a series of time-stamped data points containing the detected conditions. In step 318, user's biometric state is generated as an event set for further processing.

Figure 4:
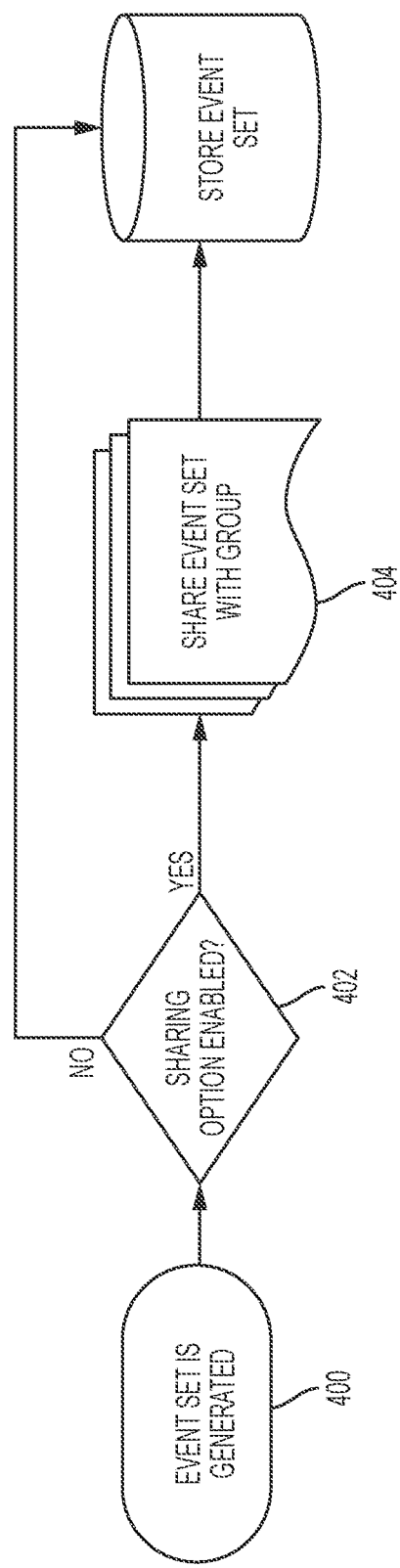
FIG. 4 illustrates an algorithm detailing a process flow enabled by the system of FIG. 1 for enabling a sharing option, in accordance with embodiments of the present invention.

FIG. 4 illustrates an algorithm detailing a process flow enabled by system 100 of FIG. 1 for enabling a sharing option, in accordance with embodiments of the present invention. In step 400, an event set is generated. In step 402, an enabled a sharing action is triggered and in step 404, event sets are shared between users. The shared event sets are store in step 408.

Figure 5:
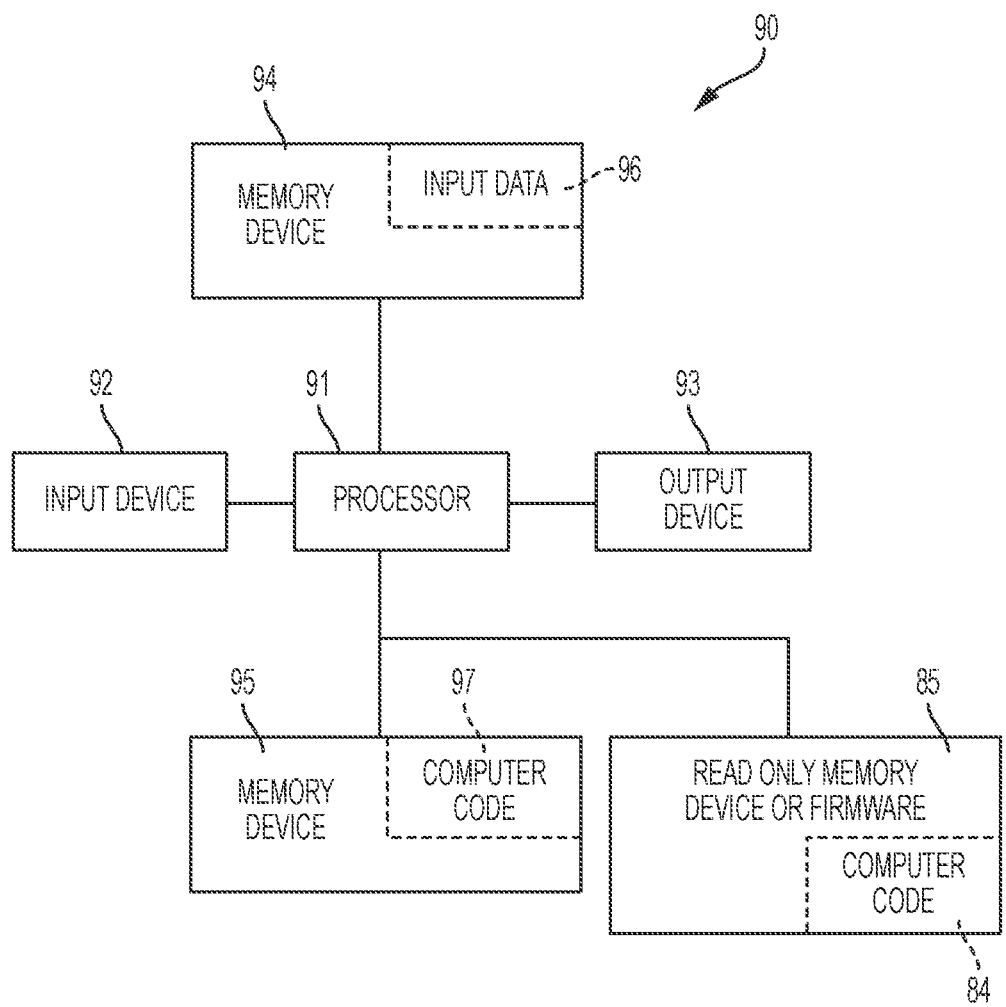
FIG. 5 illustrates a computer system used by the system of FIG. 1 for improving wearable device hardware and software technology associated with sensor triggered events by automatically retrieving sensor based data and executing a machine based interaction modification event resulting in a reduction of an elevated biometric state of a user, in accordance with embodiments of the present invention.

FIG. 5 illustrates a computer system 90 (e.g., server hardware device 23 and wearable hardware devices 14a . . . 14n of FIG. 1) used by or comprised by the system of FIG. 1 for improving wearable device hardware and software technology associated with sensor triggered events by automatically retrieving sensor based data and executing a machine based interaction modification event resulting in a reduction of an elevated biometric state of a user thereby improving a current biometric state of the user, in accordance with embodiments of the present invention.

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++, spark, R language, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 5 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithms of FIGS. 2-4) for improving wearable device hardware and software technology associated with sensor triggered events by automatically retrieving sensor based data and executing a machine based interaction modification event resulting in a reduction of an elevated biometric state of a user thereby improving a current biometric state of the user. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices Such as read only memory device 85) may include algorithms (e.g., the algorithms of FIGS. 2-4) and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including algorithms) may be stored on a static, nonremovable, read-only storage medium such as a Read-Only Memory (ROM) device 85, or may be accessed by processor 91 directly from such a static, nonremovable, read-only medium 85. Similarly, in some embodiments, stored computer program code 97 may be stored as computer-readable firmware 85, or may be accessed by processor 91 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to improve wearable device hardware and software technology associated with sensor triggered events by automatically retrieving sensor based data and executing a machine based interaction modification event resulting in a reduction of an elevated biometric state of a user thereby improving a current biometric state of the user. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for improving wearable device hardware and software technology associated with sensor triggered events by automatically retrieving sensor based data and executing a machine based interaction modification event resulting in a reduction of an elevated biometric state of a user thereby improving a current biometric state of the user. In another embodiment, the invention provides a business method that performs the process steps of the invention on a subscription, advertising, and/or fee basis. That is, a service supplier, such as a Solution Integrator, could offer to enable a process for improving wearable device hardware and software technology associated with sensor triggered events by automatically retrieving sensor based data and executing a machine based interaction modification event resulting in a reduction of an elevated biometric state of a user thereby improving a current biometric state of the user. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 5 shows the computer system 90 as a particular configuration of hardware and software, any configuration of hardware and software, as would be known to a person of ordinary skill in the art, may be utilized for the purposes stated supra in conjunction with the particular computer system 90 of FIG. 5. For example, the memory devices 94 and 95 may be portions of a single memory device rather than separate memory devices.

Cloud Computing Environment

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
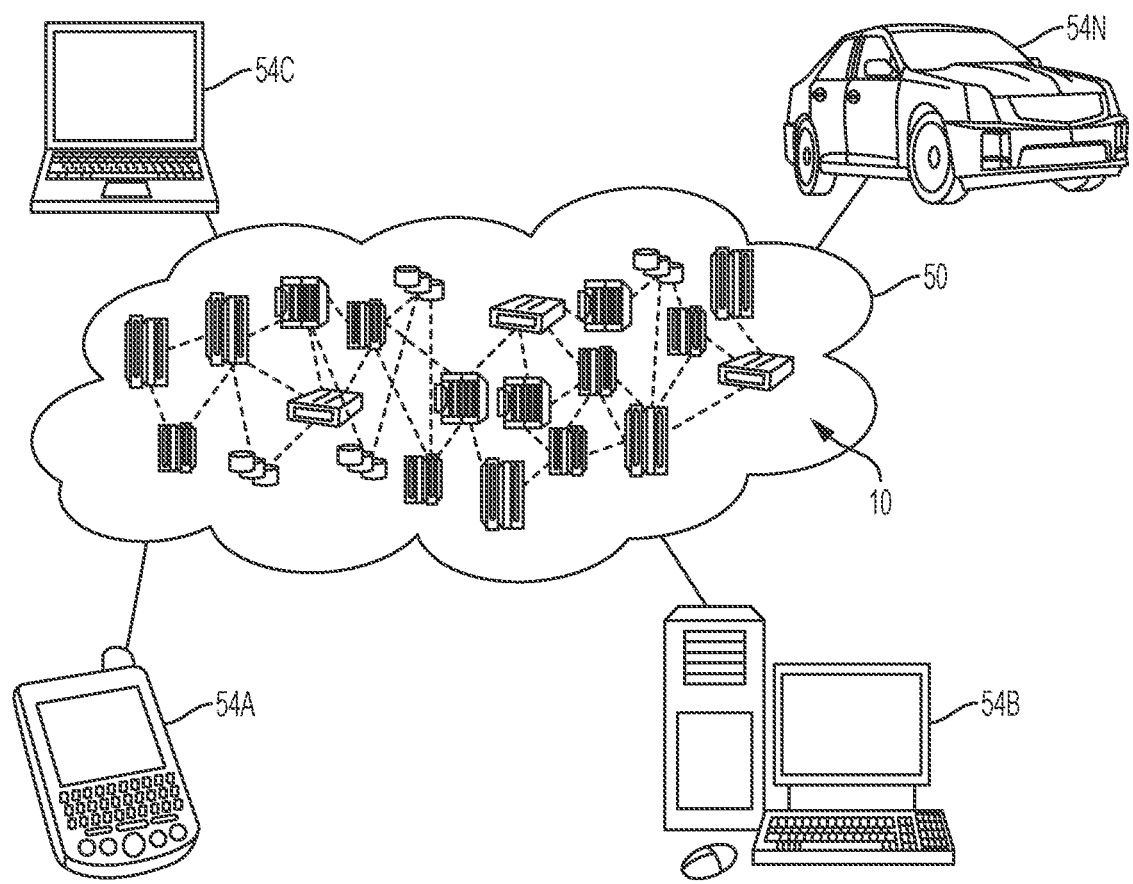
FIG. 6 illustrates a cloud computing environment, in accordance with embodiments of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 6 are intended to be illustrative only and that computing nodes 10 and cloud computing environment 50 can communicate with any type of computerized device over any type of network and/or network addressable connection (e.g., using a web browser).

Figure 7:
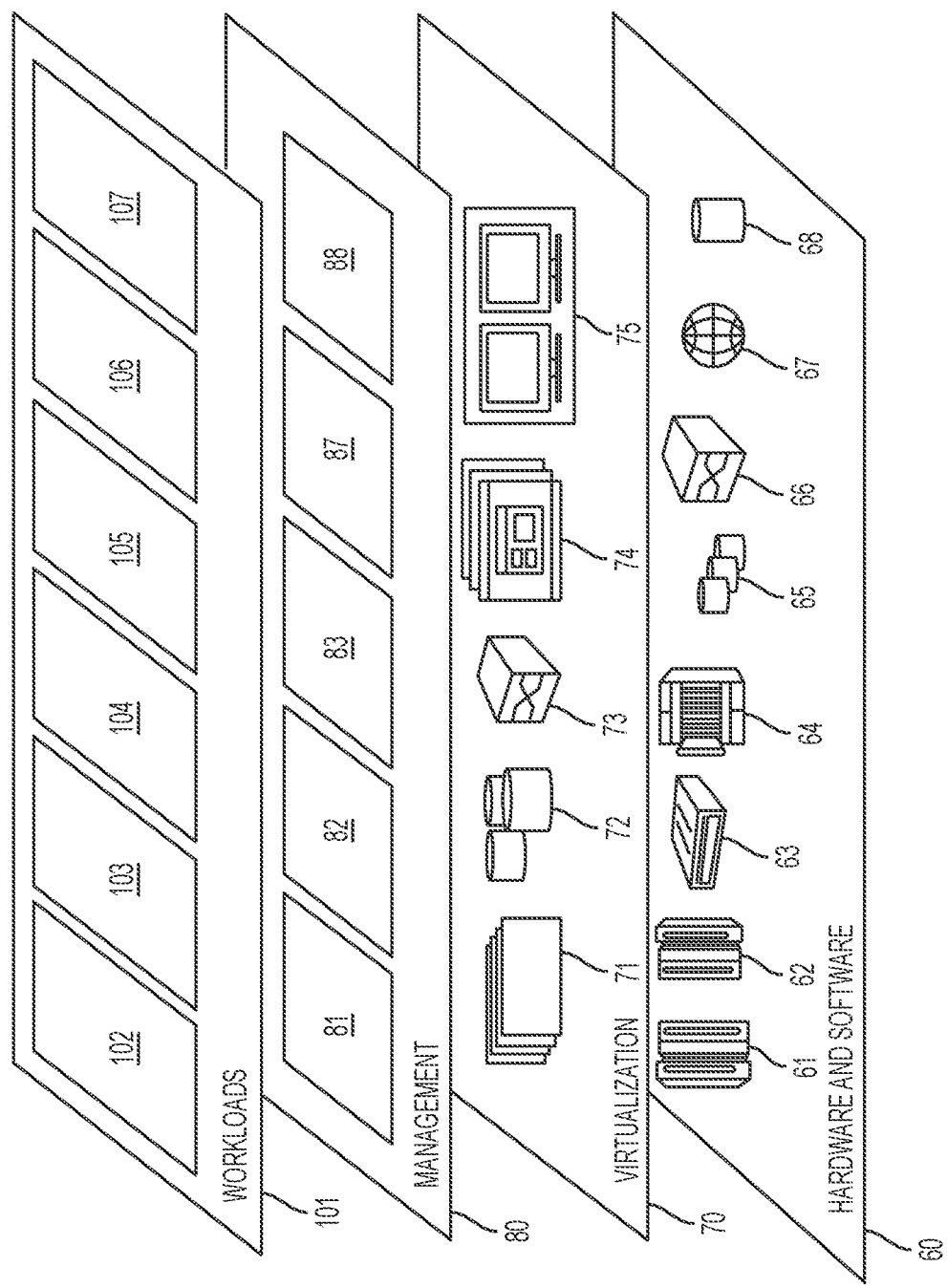
FIG. 7 illustrates a set of functional abstraction layers provided by cloud computing environment, in accordance with embodiments of the present invention.

Referring now to FIG. 7, a set of functional abstraction layers provided by cloud computing environment 50 (see FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 87 provides cloud computing resource allocation and management such that required service levels are met. Service Level Agreement (SLA) planning and fulfillment 88 provide pre-arrangement for, and procurement of, cloud computing resources for which a future requirement is anticipated in accordance with an SLA.

Workloads layer 101 provides examples of functionality for which the cloud computing environment may be utilized. Examples of workloads and functions which may be provided from this layer include: mapping and navigation 102; software development and lifecycle management 103; virtual classroom education delivery 104; data analytics processing 105; transaction processing 106; and improving wearable device hardware and software technology associated with sensor triggered events by automatically retrieving sensor based data and executing a machine based interaction modification event resulting in a reduction of an elevated biometric state of a user thereby improving a current biometric state of the user 107.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method comprising:
retrieving in real time, by a processor of a wearable hardware device via an audio/video retrieval device of said wearable hardware device, audio/video data associated with a user participating in a meeting at a location, wherein robotic devices are participants in said meeting;
retrieving in real time, by said processor via biometric sensors of said wearable hardware device, biometric data associated with a current physiological state associated with said user;
capturing, by said processor via sensors, real time group formation dynamics and detailed personal interactions of said user with respect to individuals participating in said meeting;
presenting, by said processor, to said users and said robotic devices suggestions associated with learning from captured user behavior and virtually modeled presentations;
retrieving in real time, by said processor via environmental sensors of said wearable hardware device, environmental data associated with said location of said user;
analyzing, by said processor, said audio/video data, said biometric data, said real time group formation dynamics and detailed personal interactions and said environmental data;
comparing, by said processor, said current physiological state of said user to a baseline physiological state of said user;
determining, by said processor based on results of said comparing, that said current physiological state of said user comprises an elevated physiological state with respect to said baseline physiological state of said user;
generating, by said processor, digital data associated with said audio/video data, said biometric data, said environmental data, and results indicating that said current physiological state of said user comprises said elevated physiological state;
generating, by said processor, self-learning software code for executing a machine based interaction modification event associated with reducing said elevated physiological state of said user with respect to said suggestions and said current physiological state experienced during a given timeframe, by said user or a robotic cognitive agent of said robotic devices;
executing, by said processor executing said self-learning software code, said machine based interaction modification event, wherein said executing said machine based interaction modification event comprises:
  generating a virtual simulation associated with said user and said current physiological state presented within said audio/video data, wherein said virtual simulation comprises a presentation mimicking positive interactions of said user with respect to said individuals; and
  presenting and pausing, via a GUI of said wearable hardware device, said virtual simulation to said user thereby suggesting that said user modify communication attributes of said user and proceed to participate in said meeting at said location with respect to said communication attributes being modified;
automatically modifying in response to said executing said machine based interaction modification event, by said processor, a temperature control setpoint for an HVAC system and a lighting level at said location; and
second presenting, by said processor, said virtual simulation in response to vital signs of said user being detected at normal levels.

2. The method of claim 1, wherein said biometric data associated with said user comprises attributes of the user selected from the group consisting of a current respiration rate of said user, a current body temperature of said user, a current perspiration rate of said user, and a current heartrate of said user.

3. The method of claim 1, wherein said environmental data associated with said user comprises environmental conditions of said specified location selected from the group consisting of noise level conditions, temperature level conditions, lighting level conditions, and humidity level conditions.

4. The method of claim 1, wherein said analyzing comprises executing gaussian mixture model software code with respect to said audio/video data and said biometric data.

5. The method of claim 1, wherein said analyzing comprises executing hidden markov model software code with respect to said audio/video data, said biometric data, and said environmental data.

6. The method of claim 1, wherein said executing said machine based interaction modification event comprises:
generating recommendations for said user to reduce said elevated physiological state; and
presenting, to said user via a specialized GUI, said recommendations.

7. The method of claim 1, wherein said executing said machine based interaction modification event comprises:
generating a visual simulation associated with said audio/video data; and
presenting, to said user via a specialized GUI, said visual simulation for enabling said user to reduce said elevated physiological state.

8. The method of claim 7, wherein said visual simulation comprises a virtual simulation.

9. The method of claim 1, wherein said executing said machine based interaction modification event comprises:
automatically modifying a temperature control setpoint for an HVAC system at said location of said user.

10. The method of claim 1, wherein said executing said machine based interaction modification event comprises:
automatically modifying a lighting level at said location of said user.

11. The method of claim 1, further comprising:
providing at least one support service for at least one of creating, integrating, hosting, maintaining, and deploying computer-readable code in the control hardware, said code being executed by the computer processor to implement: said retrieving said audio/video data, said retrieving said biometric data, said retrieving said environmental data, said analyzing, said determining said current biometric state, said comparing, said determining that said current biometric state of said user comprises said elevated biometric state, said generating, and said executing.

12. A computer program product, comprising a computer readable hardware storage device storing a computer readable program code, said computer readable program code comprising an algorithm that when executed by a processor of a wearable hardware device implements an automated method, said method comprising:
retrieving in real time, by said processor via an audio/video retrieval device of said wearable hardware device, audio/video data associated with a user participating in a meeting at a location, wherein robotic devices are participants in said meeting;

retrieving in real time, by said processor via biometric sensors of said wearable hardware device, biometric data associated with a current physiological state associated with said user;

capturing, by said processor via sensors, real time group formation dynamics and detailed personal interactions of said user with respect to individuals participating in said meeting;

presenting, by said processor, to said users and said robotic devices suggestions associated with learning from captured user behavior and virtually modeled presentations;

retrieving in real time, by said processor via environmental sensors of said wearable hardware device, environmental data associated with said location of said user;

analyzing, by said processor, said audio/video data, said biometric data, said real time group formation dynamics and detailed personal interactions and said environmental data;

comparing, by said processor, said current physiological state of said user to a baseline physiological state of said user;

determining, by said processor based on results of said comparing, that said current physiological state of said user comprises an elevated physiological state with respect to said baseline physiological state of said user;

generating, by said processor, digital data associated with said audio/video data, said biometric data, said environmental data, and results indicating that said current physiological state of said user comprises said elevated physiological state;

generating, by said processor, self-learning software code for executing a machine based interaction modification event associated with reducing said elevated physiological state of said user with respect to said suggestions and said current physiological state experienced during a given timeframe, by said user or a robotic cognitive agent of said robotic devices;

executing, by said processor executing said self-learning software code, said machine based interaction modification event, wherein said executing said machine based interaction modification event comprises:

generating a virtual simulation associated with said user and said current physiological state presented within said audio/video data, wherein said virtual simulation comprises a presentation mimicking positive interactions of said user with respect to said individuals; and presenting and pausing, via a GUI of said wearable hardware device, said virtual simulation to said user thereby suggesting that said user modify communication attributes of said user and proceed to participate in said meeting at said location with respect to said communication attributes being modified;

automatically modifying in response to said executing said machine based interaction modification event, by said processor, a temperature control setpoint for an HVAC system and a lighting level at said location; and second presenting, by said processor, said virtual simulation in response to vital signs of said user being detected at normal levels.

13. The computer program product of claim 12, wherein said biometric data associated with said user comprises attributes of the user selected from the group consisting of a current respiration rate of said user, a current body temperature of said user, a current perspiration rate of said user, and a current heartrate of said user.

14. The computer program product of claim 12, wherein said environmental data associated with said user comprises environmental conditions of said specified location selected from the group consisting of noise level conditions, temperature level conditions, lighting level conditions, and humidity level conditions.

15. The computer program product of claim 12, wherein said analyzing comprises executing gaussian mixture model software code with respect to said audio/video data and said biometric data.

16. The computer program product of claim 12, wherein said analyzing comprises executing hidden markov model software code with respect to said audio/video data, said biometric data, and said environmental data.

17. The computer program product of claim 12, wherein said executing said machine based interaction modification event comprises:

generating recommendations for said user to reduce said elevated physiological state; and presenting, to said user via a specialized GUI, said recommendations.

18. The computer program product of claim 12, wherein said executing said machine based interaction modification event comprises:

generating a visual simulation associated with said audio/video data; and presenting, to said user via a specialized GUI, said visual simulation for enabling said user to reduce said elevated physiological state.

19. The computer program product of claim 18, wherein said visual simulation comprises a virtual simulation.

20. A wearable hardware device comprising a processor coupled to a computer-readable memory unit, said memory unit comprising instructions that when executed by the computer processor implements an automated method comprising:

retrieving in real time, by said processor via an audio/video retrieval device of said wearable hardware device, audio/video data associated with a user participating in a meeting at a location, wherein robotic devices are participants in said meeting;

retrieving in real time, by said processor via biometric sensors of said wearable hardware device, biometric data associated with a current physiological state associated with said user;

capturing, by said processor via sensors, real time group formation dynamics and detailed personal interactions of said user with respect to individuals participating in said meeting;

presenting, by said processor, to said users and said robotic devices suggestions associated with learning from captured user behavior and virtually modeled presentations;

retrieving in real time, by said processor via environmental sensors of said wearable hardware device, environmental data associated with said location of said user;

analyzing, by said processor, said audio/video data, said biometric data, said real time group formation dynamics and detailed personal interactions and said environmental data;

comparing, by said processor, said current physiological state of said user to a baseline physiological state of said user;

determining, by said processor based on results of said comparing, that said current physiological state of said user comprises an elevated physiological state with respect to said baseline physiological state of said user;
generating, by said processor, digital data associated with said audio/video data, said biometric data, said environmental data, and results indicating that said current physiological state of said user comprises said elevated physiological state;
generating, by said processor, self-learning software code for executing a machine based interaction modification event associated with reducing said elevated physiological state of said user with respect to said suggestions and said current physiological state experienced during a given timeframe, by said user or a robotic cognitive agent of said robotic devices;
executing, by said processor executing said self-learning software code, said machine based interaction modification event, wherein said executing said machine based interaction modification event comprises:
  generating a virtual simulation associated with said user and said current physiological state presented within said audio/video data, wherein said virtual simulation comprises a presentation mimicking positive interactions of said user with respect to said individuals; and
  presenting and pausing, via a GUI of said wearable hardware device, said virtual simulation to said user thereby suggesting that said user modify communication attributes of said user and proceed to participate in said meeting at said location with respect to said communication attributes being modified;
automatically modifying in response to said executing said machine based interaction modification event, by said processor, a temperature control setpoint for an HVAC system and a lighting level at said location; and
second presenting, by said processor, said virtual simulation in response to vital signs of said user being detected at normal levels.

* * * * *